(12) United States Patent
Pillow et al.

(10) Patent No.: US 10,396,287 B2
(45) Date of Patent: Aug. 27, 2019

(54) AMINO FLUORENE MONOMERS, POLYMERS, AND ORGANIC ELECTRONIC DEVICES

(71) Applicants: Sumitomo Chemical Company Limited, Tokyo (JP); Cambridge Display Technology Limited, Godmanchester (GB)

(72) Inventors: Jonathan Pillow, Godmanchester (GB); Richard J. Wilson, Godmanchester (GB); Sophie Barbara Heidenhain, Lower Cambourne (GB); Ruth Pegington, Godmanchester (GB); Alexander Doust, Godmanchester (GB); Richard Owoare, Cambridge (GB)

(73) Assignees: Sumitomo Chemical Company Limited, Tokyo (JP); Cambridge Display Technology Limited, Godmanchester (GB)

( * ) Notice: Subject to any disclaimer, the term of this patent is extended or adjusted under 35 U.S.C. 154(b) by 1309 days.

(21) Appl. No.: 14/372,534

(22) PCT Filed: Jan. 16, 2013

(86) PCT No.: PCT/GB2013/050089
§ 371 (c)(1),
(2) Date: Jul. 16, 2014

(87) PCT Pub. No.: WO2013/108023
PCT Pub. Date: Jul. 25, 2013

(65) Prior Publication Data
US 2015/0060798 A1    Mar. 5, 2015

(30) Foreign Application Priority Data

Jan. 16, 2012 (GB) .................................. 1200619.3
May 16, 2012 (GB) .................................. 1208610.4

(51) Int. Cl.
*C07C 211/61*    (2006.01)
*C08G 61/12*    (2006.01)
(Continued)

(52) U.S. Cl.
CPC ........ *H01L 51/0043* (2013.01); *C07C 211/61* (2013.01); *C08G 61/12* (2013.01); *C08G 73/026* (2013.01); *C09K 11/06* (2013.01); *H01L 51/0039* (2013.01); *H01L 51/5056* (2013.01); *H01L 51/5203* (2013.01); *C07C 2603/18* (2017.05); *C08G 2261/135* (2013.01); *C08G 2261/148* (2013.01); *C08G 2261/1412* (2013.01); *C08G 2261/314* (2013.01); *C08G 2261/3142* (2013.01); *C08G 2261/3162* (2013.01); *C08G 2261/3245* (2013.01); *C08G 2261/411* (2013.01); *C08G 2261/512* (2013.01); *C08G 2261/76* (2013.01); *C08G 2261/95* (2013.01); *C09K 2211/1011* (2013.01); *C09K 2211/1014* (2013.01); *C09K 2211/1416* (2013.01); *C09K 2211/1433* (2013.01); *C09K 2211/185* (2013.01)

(58) Field of Classification Search
CPC combination set(s) only.
See application file for complete search history.

(56) References Cited

U.S. PATENT DOCUMENTS 7,651,746 B2 * 1/2010 Hudack .................. C07C 211/58
428/32.23
9,859,499 B2 * 1/2018 Pegington ........... H01L 51/0043
(Continued)

FOREIGN PATENT DOCUMENTS

EP    0 879 868 A2    11/1988
EP    0 879 868 A3    1/1999
(Continued)

OTHER PUBLICATIONS

U.S. Appl. No. 14/909,045, filed Jan. 2016, Heidenhain; Sophie.*
Sekiguchi et al. "Sulfonated polymeric compound, its intermediate, and organic electroluminescent device containing the compound " WO 2008/126393A1 (pub. Jul. 22, 2010). English machine translation obtained from Espacenet of equivalent family member JP5372742. (Year: 2010).*
International Search Report and Written Opinion for International Application No. PCT/GB2013/050089 dated Jun. 24, 2013.
International Preliminary Report on Patentability for International Application No. PCT/GB2013/050089 dated Jul. 31, 2014.
(Continued)

*Primary Examiner* — Amanda L Aguirre
(74) *Attorney, Agent, or Firm* — Wolf, Greenfield & Sacks, P.C.

(57) ABSTRACT

An organic electronic device comprising an anode, a cathode, a semiconducting layer between the anode and the cathode and a hole transporting layer between the anode and the semiconducting layer, the hole-transporting layer comprising a co-polymer comprising repeat units of formula (I) and one or more co-repeat units: (I) wherein: $Ar^1$ independently in each occurrence represents a fused aryl or fused heteroaryl group that may be unsubstituted or substituted with one or more substituents; $Ar^2$ represents an aryl or heteroaryl group that may be unsubstituted or substituted with one or more substituents; R independently in each occurrence represents a substituent; and m is 1 or 2, preferably 1; and each $Ar^1$ is directly bound to an aromatic or heteroaromatic group of a co-repeat unit.

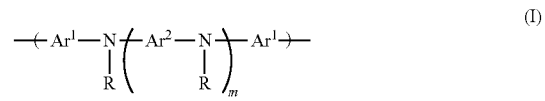

(I)

13 Claims, 1 Drawing Sheet

(51) Int. Cl.
*C08G 73/02* (2006.01)
*C09K 11/06* (2006.01)
*H01L 51/00* (2006.01)
*H01L 51/50* (2006.01)
*H01L 51/52* (2006.01)

(56) References Cited

U.S. PATENT DOCUMENTS

| | | | | |
|---|---|---|---|---|
| 9,966,534 | B2 * | 4/2018 | Stackhouse | H01L 51/0035 428/690 |
| 2004/0262574 | A1 | 12/2004 | Suzuki et al. | |
| 2007/0096082 | A1 * | 5/2007 | Gaynor | C07C 211/60 257/40 |
| 2009/0200926 | A1 * | 8/2009 | Lee | C07C 211/61 313/504 |

FOREIGN PATENT DOCUMENTS

| | | | | |
|---|---|---|---|---|
| EP | 1 985 643 | A1 | | 10/2008 |
| EP | 2 112 184 | A1 | | 10/2009 |
| EP | 2 112 185 | A1 | | 10/2009 |
| EP | 2112184 | A1 * | | 10/2009 ............ C08G 61/12 |
| EP | 2 159 245 | A1 | | 3/2010 |
| GB | 2 447 173 | A | | 9/2008 |
| JP | 11-185965 | | | 7/1999 |
| JP | 2001-166519 | | | 6/2001 |
| JP | 2001-226331 | | | 8/2001 |
| JP | 2002-040686 | | | 2/2002 |
| JP | 2004-212959 | | | 7/2004 |
| JP | 2005-062301 | A | | 3/2005 |
| JP | 2005 169781 | | | 6/2005 |
| JP | 2009 016739 | | | 1/2009 |
| JP | 2010-037312 | | | 2/2010 |
| WO | WO 00/55927 | A1 | | 9/2000 |
| WO | WO 02/051958 | A1 | | 7/2002 |
| WO | WO 2005049546 | A1 * | | 6/2005 ............ C07C 211/58 |
| WO | WO 2005/104263 | A1 | | 11/2005 |
| WO | WO 2007/071969 | A2 | | 6/2007 |
| WO | WO 2008/120470 | A1 | | 10/2008 |
| WO | WO-2008126393 | A1 * | | 10/2008 ............ C08G 61/126 |

OTHER PUBLICATIONS

Office Communication dated Apr. 25, 2012 for Great Britain Application No. GB1200619.3.
Office Communication dated Aug. 20, 2012 for Great Britain Application No. GB1200619.3.
Office Communication dated Sep. 27, 2012 for Great Britain Application No. GB1208610.4.
Belfield et al., New highly efficient two-photon fluorescent dyes. Proceedings of SPIE. 2004;5351:173-80.
Hreha et al., Synthesis of acrylate and norbornene polymers with pendant 2,7-bis(diarylamino)fluorene hole-transport groups. Tetrahedron. 2004;60(34):7169-76.
[No Author Listed] a Dictionary of Science. Fifth Edition. Oxford University Press (2005). 786-787.
[No Author Listed] IUPAC. Compendium of Chemical Terminology, 2nd ed. (the "Gold Book"). Compiled by A. D. McNaught and A. Wilkinson. Blackwell Scientific Publications, Oxford (1997). XML on-line https://goldbook.iupac.org/html/S/506076.html. corrected version: http://goldbook.iupac.org (2006-) created by M. Nic, J. Jirat, B. Kosata; updates compiled by A. Jenkins. ISBN 0-9678550-9-8. https://doi.org/10.1351/goldbook. Last update: Feb. 24, 2014; version: 2.3.3. 2 pages.

* cited by examiner

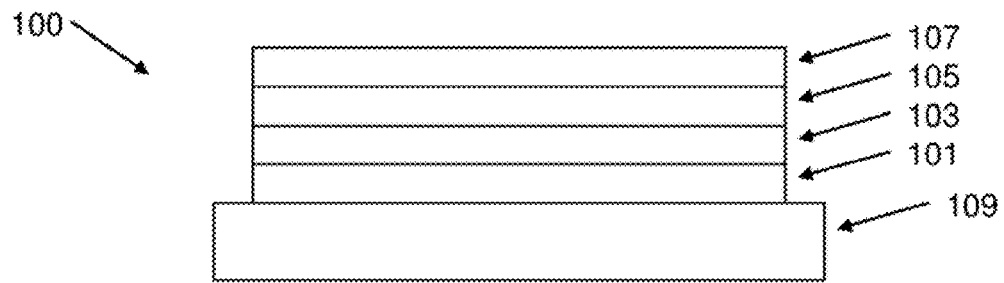

AMINO FLUORENE MONOMERS, POLYMERS, AND ORGANIC ELECTRONIC DEVICES

RELATED APPLICATIONS

The present application is a national stage filing under 35 U.S.C. § 371 of international PCT application, PCT/GB2013/050089, filed Jan. 16, 2013, which claims priority to United Kingdom patent application, GB 1200619.3, filed Jan. 16, 2012, and United Kingdom patent application, GB 1208610.4, filed May 16, 2012, each of which is incorporated herein by reference.

BACKGROUND OF THE INVENTION

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

Suitable light-emitting materials include small molecule, polymeric and dendrimeric materials. Suitable light-emitting polymers include poly(arylene vinylenes) such as poly (p-phenylene vinylenes) and polyarylenes such as polyfluorenes.

A light emitting layer may comprise a semiconducting host material and a light-emitting dopant wherein energy is transferred from the host material to the light-emitting dopant. For example, J. Appl. Phys. 65, 3610, 1989 discloses a host material doped with a fluorescent light-emitting dopant (that is, a light-emitting material in which light is emitted via decay of a singlet exciton).

Phosphorescent dopants are also known (that is, a light-emitting dopant in which light is emitted via decay of a triplet exciton).

A hole-transporting layer may be provided between the anode and light-emitting layer of an OLED.

WO 2009/067419 discloses compounds having formula I, formula II or formula III:

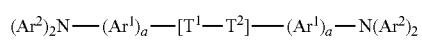

(I)

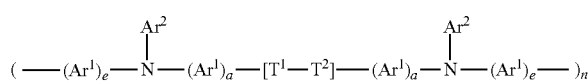

(II)

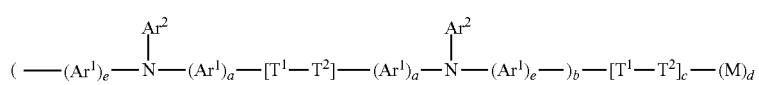

(III)

T1 and T2 are conjugated moieties which are connected in a non-planar configuration. WO 2009/084548 discloses polymers comprising a repeating unit A and a repeat unit B, wherein A is selected from divalent groups derived from compounds represented by formula (1):

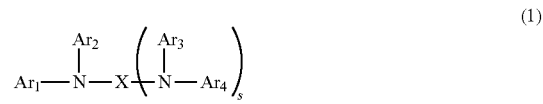

(1)

wherein $Ar_1$ to $Ar_4$ are each independently a substituted or unsubstituted aryl group having 6 to 40 ring-forming carbon atoms, a substituted or unsubstituted heterocyclic group having 3 to 40 ring-forming atoms, or a substituted or unsubstituted alkyl group having 1 to 50 carbon atoms;

X is a substituted or unsubstituted aryl group having 6 to 40 ring-forming carbon atoms, a substituted or unsubstituted heterocyclic group having 3 to 40 ring-forming atoms, or a substituted or unsubstituted styrene-derived group; and s is an integer of 0 to 3.

EP 2233508 discloses polymers comprising a repeating unit A and a repeat unit B, wherein A includes divalent groups derived from compounds represented by formulas (1) to (4):

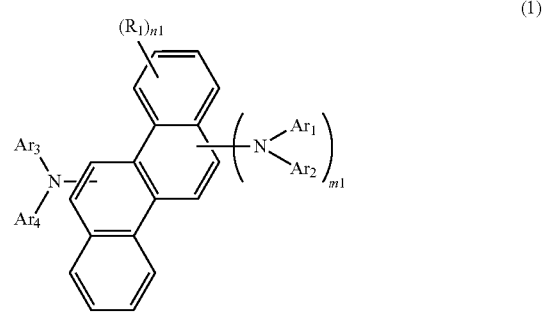

(1)

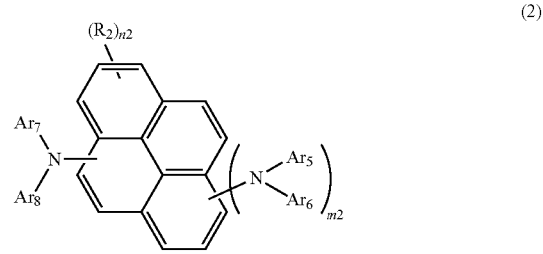

(2)

-continued

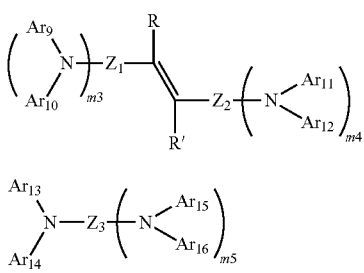

(3)

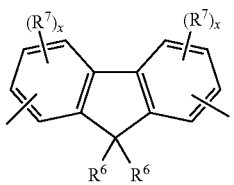

(4)

EP 2272894 discloses a polymer formed by polymerization of the following monomers:

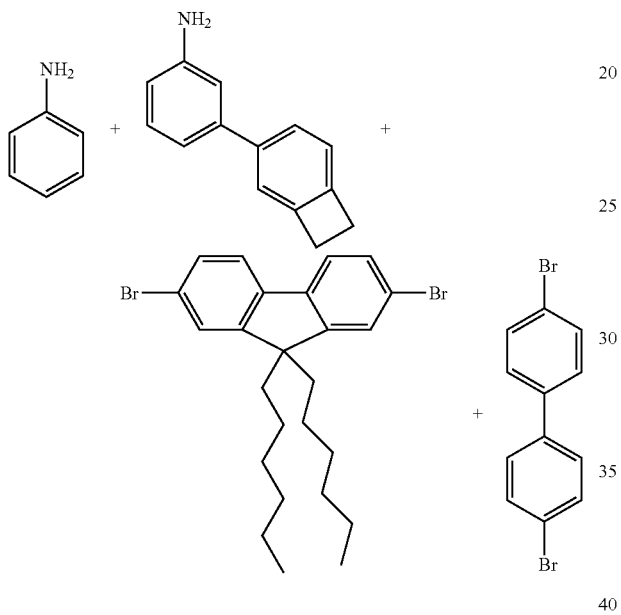

SUMMARY OF THE INVENTION

In a first aspect the invention provides an organic electronic device comprising an anode, a cathode, a semiconducting layer between the anode and the cathode and a hole transporting layer between the anode and the semiconducting layer, the hole-transporting layer comprising a co-polymer comprising repeat units of formula (I) and one or more co-repeat units:

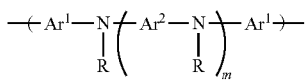

(I)

wherein:

$Ar^1$ independently in each occurrence represents a fused aryl or fused heteroaryl group that may be unsubstituted or substituted with one or more substituents; $Ar^2$ represents an aryl or heteroaryl group that may be unsubstituted or substituted with one or more substituents; R independently in each occurrence represents a substituent; and m is 1 or 2, preferably 1; and each $Ar^1$ is directly bound to an aromatic or heteroaromatic group of a co-repeat unit.

Optionally, R is an aryl or heteroaryl group that may be unsubstituted or substituted with one or more substituents.

Optionally, each $Ar^1$ is a fused aryl.

Optionally, each $Ar^1$ comprises at least six $sp^2$ hybridised atoms, optionally at least eight $sp^2$ hybridised atoms, spacing the N atom bound to each $Ar^1$ from an adjacent repeat unit.

Optionally, $Ar^2$ is a fused aryl.

Optionally, at least one of $Ar^1$ and $Ar^2$ has formula (II):

(II)

wherein $R^6$ in each occurrence is independently H or a substituent; $R^7$ in each occurrence is independently a substituent; and x in each occurrence is independently 0, 1, 2 or 3.

Optionally, each $R^6$ and, where present, each $R^7$ is independently a hydrocarbyl, preferably a $C_{1-40}$ hydrocarbyl.

Optionally, the polymer comprises at least two different co-repeat units.

Optionally, at least one co-repeat unit is an aromatic group that may be unsubstituted or substituted with one or more substituents.

Optionally, at least one of the co-repeat units is a repeat unit of formula (III):

$$\text{(III)}$$

wherein p in each occurrence is independently 0, 1, 2, 3 or 4, optionally 1 or 2; n is 1, 2 or 3; and $R^1$ independently in each occurrence is a substituent.

Optionally, at least one of the co-repeat units is a repeat unit of formula (IV):

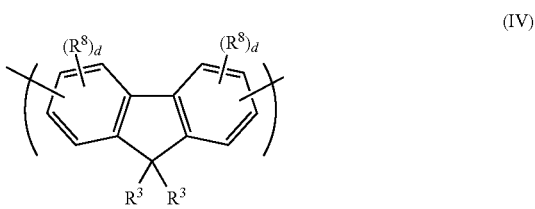

(IV)

wherein $R^3$ in each occurrence is the same or different and is H or a substituent, and wherein the two groups $R^3$ may be linked to form a ring; $R^8$ is a substituent; and d is 0, 1, 2 or 3.

Optionally, the co-polymer is crosslinked.

Optionally, the co-polymer is crosslinked through a crosslinking substituent of a repeat unit of the polymer.

Optionally, the device is an organic light-emitting device, and the semiconducting layer is an organic light-emitting layer.

Optionally, the light-emitting layer comprises a fluorescent blue light-emitting material.

Optionally, the light-emitting layer comprises a phosphorescent light-emitting material.

Optionally, the light-emitting layer comprises a green phosphorescent light-emitting material.

Optionally, $Ar^1$ is not phenanthrene.

In a second aspect the invention provides a method of forming an organic electronic device according to the first aspect, the method comprising the steps of: forming the hole-transporting layer over the anode; forming the semiconducting layer over the hole-transporting layer; and forming the cathode over the semiconducting layer.

Optionally according to the second aspect, the hole transporting layer is formed by depositing a formulation comprising the polymer comprising repeat units of formula (I) and one or more solvents and evaporating the one or more solvents.

Optionally according to the second aspect, the hole-transporting layer is crosslinked prior to formation of the semiconducting layer.

In a third aspect, the invention provides a co-polymer comprising repeat units of formula (VII) and one or more co-repeat units

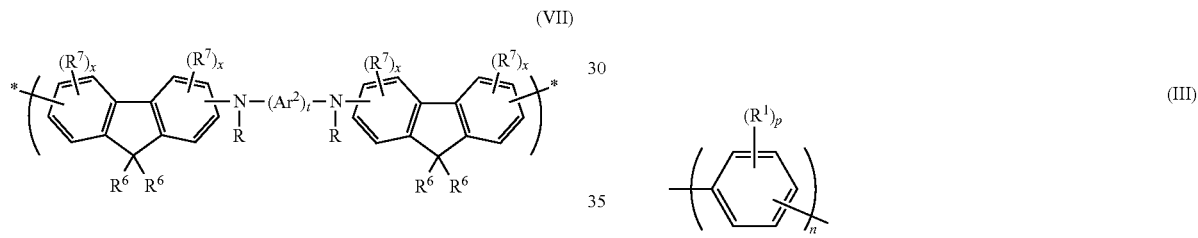

wherein:

$Ar^2$ represents an aryl or heteroaryl group that may be unsubstituted or substituted with one or more substituents; R independently in each occurrence represents a substituent; $R^6$ independently in each occurrence represents a substituent; $R^7$ in each occurrence is independently a substituent; x in each occurrence is independently 0, 1, 2 or 3; t is at least 1, optionally 1 or 2; and * represents a point of attachment of the repeat unit of formula (VII) to adjacent repeat units; and the repeat units of formula (VII) are directly bound through each point of attachment to an aromatic or heteroaromatic group of a co-repeat unit.

Optionally according to the third aspect, the repeat units of formula (VII) have formula (VIIa):

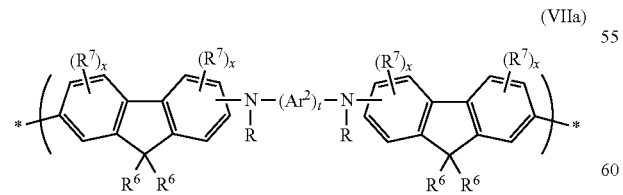

Optionally according to the third aspect, R is an aryl or heteroaryl group that may be unsubstituted or substituted with one or more substituents.

Optionally according to the third aspect, $Ar^2$ is a fused aryl.

Optionally according to the third aspect, $Ar^2$ has formula (II):

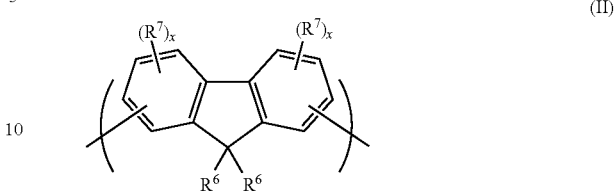

wherein $R^6$ in each occurrence is independently H or a substituent.

Optionally according to the third aspect, each $R^6$ is independently a hydrocarbyl, preferably a $C_{1-40}$ hydrocarbyl.

Optionally according to the third aspect, wherein the polymer comprises repeat units of formula (VII) and at least two different co-repeat units.

Optionally according to the third aspect, the polymer comprises a co-repeat unit of formula (III):

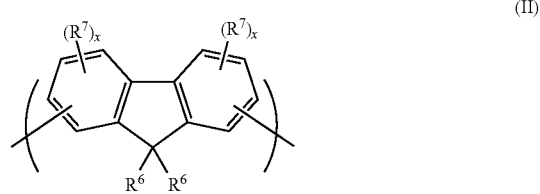

wherein p in each occurrence is independently 0, 1, 2, 3 or 4, optionally 1 or 2; n is 1, 2 or 3; and $R^1$ independently in each occurrence is a substituent.

Optionally according to the third aspect, the polymer comprises a repeat unit of formula (IV):

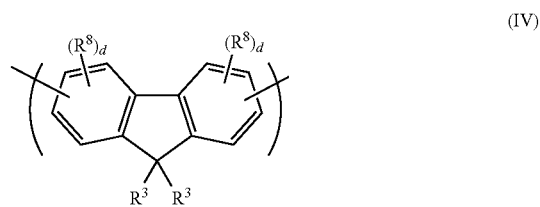

wherein $R^3$ in each occurrence is the same or different and is H or a substituent, and wherein the two groups $R^3$ may be linked to form a ring; $R^8$ is a substituent; and d is 0, 1, 2 or 3.

Optionally according to the third aspect, the polymer comprises crosslinkable substituents.

Optionally according to the third aspect, the co-polymer is crosslinked through a crosslinking substituent of a repeat unit of the co-polymer.

In a fourth aspect, the invention provides a monomer of formula (VIIm):

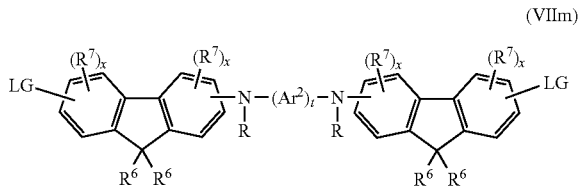

(VIIm)

wherein $Ar^2$, R, $R^6$, $R^7$, t and x are as described above, and each LG independently represents a leaving group.

Optionally according to the fourth aspect, each LG is independently selected from halogen, boronic acid; boronic acid esters; sulfonic acid; and sulfonic acid esters.

In a fifth aspect the invention provides a method of forming a polymer comprising the step of polymerising a monomer according to the fourth aspect in the presence of a metal catalyst.

Optionally according to the fifth aspect the monomer is polymerised in the presence of one or more co-monomers to form a copolymer according to the third aspect.

In a sixth aspect the invention provides an organic electronic device comprising a polymer according to the third aspect.

Optionally according to the sixth aspect the device is an organic light-emitting device.

Optionally according to the sixth aspect a light-emitting layer or hole-transporting layer of the device comprises the polymer according to the third aspect.

Optionally according to the sixth aspect a light-emitting layer of the device comprises the polymer according to the third aspect and a phosphorescent dopant blended with or bound to the polymer.

Polymers containing repeat units of formula (VII) may contain one or more further co-repeat units as described in the first aspect of the invention. $Ar^2$ of repeat units of formula (VII) may be linked as described for $Ar^2$ groups of repeat units of formula (I). Repeat units of formula (VII) may be linked to adjacent repeat units as described for repeat units of formula (I). $Ar^2$, R, m, $R^6$, $R^7$ and x of repeat units of formula (VII) may be selected from respective $Ar^2$, R, m, $R^6$, $R^7$ and x as described for repeat units of formula (I).

"Aryl" and "heteroaryl" as used herein means an unfused aryl or heteroaryl ring or a fused aryl or heteroaryl ring system.

DESCRIPTION OF THE DRAWINGS

The invention will now be described in more detail with reference to the drawings, in which:

The FIGURE illustrates an OLED according to an embodiment of the invention.

DETAILED DESCRIPTION OF THE INVENTION

The invention is described hereinafter with reference to repeat units of formula (I), however it will be appreciated that the description of repeat units of formula (I) and polymers containing repeat units of formula (I) also applies to repeat units of formula (VII) and polymers containing repeat units of formula (VII) in the case where each $Ar^1$ of formula (I) is fluorene. This applicable description includes, without limitation: linking positions of repeat units of formula (I), substituents of repeat units of formula (I), methods of processing polymers comprising repeat units of formula (I), uses of polymers comprising repeat units of formula (I), and co-repeat units of polymers containing repeat units of formula (I).

With reference to the FIGURE, an OLED 100 according to an embodiment of the invention has an anode 101, a cathode 107, a light-emitting layer 105 between the anode and the cathode, and a hole-transporting layer 103 between the anode 101 and the light-emitting layer 105. The device is supported on a substrate 109, which may be a glass or plastic substrate.

One or more further layers may be provided between the anode and the cathode, for example a hole-injection layer, an electron-blocking layer, an electron-transporting layer or an electron blocking layer. In a preferred embodiment, a hole-injection layer is provided between the anode and the hole-transporting layer. Where present, the hole-injection layer is preferably adjacent to the hole-transporting layer. Preferably, the hole-transporting layer is adjacent to the light-emitting layer.

The OLED may contain more that one light-emitting layer, for example a plurality of light-emitting layers that together produce white light.

Polymers containing repeat units of formula (I) may be used in a light-emitting layer or charge-transporting layer of an OLED. Preferably, the polymer is used in a hole-transporting layer of an OLED. If a polymer containing a repeat unit of formula (I) is used in a light-emitting layer, the device may or may not have a hole transporting layer between the anode and the light-emitting layer.

The layer containing the polymer comprising repeats unit of formula may consist essentially of that polymer or may contain one or more further components.

In the case of a phosphorescent OLED, a polymer comprising repeat units of formula (I) may be provided in a light-emitting layer containing one or more phosphorescent dopants, or may be provided in a layer adjacent to a light-emitting layer, for example a hole-transporting layer.

Quenching of phosphorescence may be caused by a material having a low triplet energy level that is in or adjacent to a phosphorescent light-emitting layer, and so the polymer may have a triplet energy level of at least 2.25 eV. This triplet energy level may avoid quenching of phosphorescent light emitted by green phosphorescent materials, which have a triplet energy level of about 2.4 eV, or quenching of light emitted by blue phosphorescent materials, which have a triplet energy level of about 2.7 eV.

The triplet energy level may be measured by Low Temperature Phosphorescence Spectroscopy [References Y. V. Romaovskii et al, Physical Review Letters, 2000, 85 (5), p 1027, A. van Dijken et al, Journal of the American Chemical Society, 2004, 126, p 7718]

Polymers comprising repeat units of formula (I) may be used as a hole-transporting layer adjacent to a fluorescent light-emitting layer. In this case, the singlet energy level of the polymer is preferably no more than 0.1 eV below that of the fluorescent light-emitting material, preferably at least the same as or higher than that of the fluorescent light-emitting material, in order to avoid quenching of fluorescent light emitted by the fluorescent light-emitting material. For a light-emitting layer containing a blue fluorescent light-emitting material, the singlet energy level of the polymer is preferably at least 2.5 eV.

The singlet energy may be measured by measuring energy of the peak of the fluorescence spectrum of the material.

The groups Ar¹ of the repeat unit of formula (I) space the N atoms of the repeat unit from adjacent repeat units.

Ar¹ may be a group of at least two aromatic or heteroaromatic rings that share a ring bond. Exemplary condensed aromatic groups include naphthalene and anthracene.

Ar¹ may be a fused group comprising two rings selected from aromatic and heteroaromatic rings that are linked by a direct bond. The fused group may contain one or more non-aromatic rings. An example is fluorene.

Ar¹ may include aromatic or heteroaromatic rings that are linked by a direct bond and aromatic or heteroaromatic rings that share a ring bond, for example benzofluorene.

Ar² may be a fused or unfused aryl or heteroaryl group. Ar² may be the same as or different from one or both of Ar¹.

Preferred groups Ar¹ and Ar² include the following:

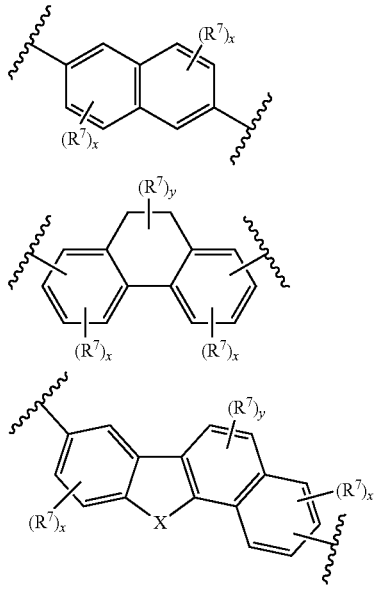

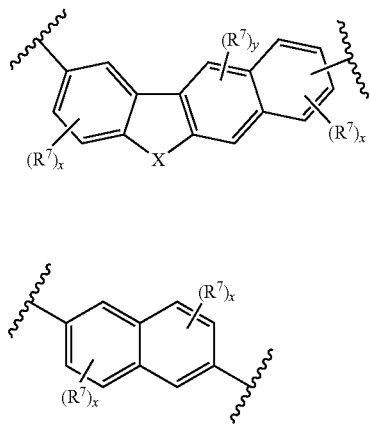

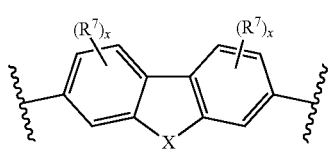

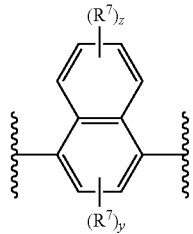

$X=CR^7{}_2, S, O, NR^7, BR^7, P=O, Si$

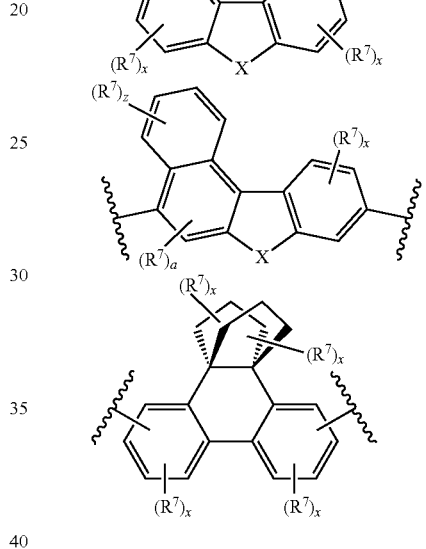

wherein $R^7$ in each occurrence is independently a substituent, optionally $C_{1-40}$ hydrocarbyl, for example $C_{1-20}$ alkyl; unsubstituted phenyl; and phenyl substituted with one or more $C_{1-20}$ alkyl groups; x in each occurrence is independently 0, 1, 2 or 3; y is 0, 1 or 2; z is 0, 1, 2, 3 or 4; and a is 0 or 1.

The groups Ar¹ of a repeat unit of formula (I) may be the same or different.

The groups R of a repeat unit of formula (I) may be the same or different. Preferred groups R are $C_{1-40}$ hydrocarbyl, for example $C_{1-20}$ alkyl; unsubstituted phenyl; and phenyl substituted with one or more $C_{1-20}$ alkyl groups.

Preferred groups Ar² include fluorene and phenylene, each of which may be substituted with one or more substituents, optionally one or more $C_{1-40}$ hydrocarbyl, optionally $C_{1-20}$ alkyl; unsubstituted phenyl; and phenyl substituted with one or more $C_{1-20}$ alkyl groups.

Where Ar¹ and/or Ar² are fluorene units of formula (II), exemplary substituents $R^6$ include $C_{1-40}$ hydrocarbyl, for example $C_{1-20}$ alkyl; unsubstituted phenyl; and phenyl substituted with one or more $C_{1-20}$ alkyl groups.

The selection of Ar¹ and/or Ar² may be used to provide a desired singlet and/or triplet energy level. For example, where Ar¹ and/or Ar² are fluorene units then one, two or all three of the fluorene units may be linked through their 3- and 6-positions to limit the extent of conjugation across the repeat unit of formula (I) as compared to repeat units of formula (I) in which fluorene units are linked through their 2- and 7-positions.

Exemplary repeat units of formula (I) include the following, each of which may be unsubstituted or substituted with one or more substituents:

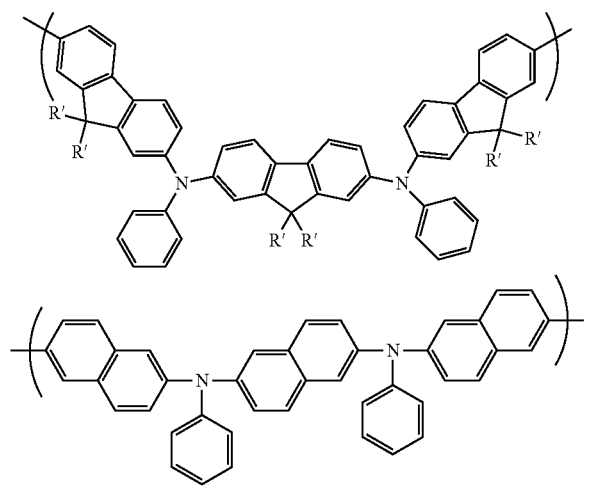

wherein R' is $C_{1-40}$ hydrocarbyl.

Co-Repeat Units

Copolymers of the invention may be block, regular or random copolymers containing repeat units of formula (I) and one or more co-repeat units.

Repeat units of formula (I) preferably make up 1-75 mol %, more preferably 10-50 mol % of repeat units of the polymer.

Co-repeat units include repeat units that are directly adjacent to repeat units of formula (I) and repeat units that are spaced apart from repeat units of formula (I). The copolymer may contain repeat units of formula (I) and adjacent co-repeat units only, or it may contain repeat units of formula (I), co-repeat units adjacent to repeat units of formula (I), and one or more further co-repeat units Exemplary co-repeat units include arylene repeat units, for example 1,2-, 1,3- and 1,4-phenylene repeat units, 3,6- and 2,7-linked fluorene repeat units, indenofluorene, naphthalene, anthracene and phenanthrene repeat units, each of which may be unsubstituted or substituted with one or more substitutents, for example one or more $C_{1-30}$ hydrocarbyl substituents.

The polymer comprising repeat units of formula (I) is preferably at least partially conjugated, and repeat units of formula (I) are preferably directly linked to aromatic or heteroaromatic groups of adjacent co-repeat units.

If used in the same layer as, or in a layer adjacent to, a light-emitting material with a high singlet or triplet energy level then the extent of conjugation along the backbone of the polymer may be limited by selection of co-repeat units. Exemplary co-repeat units that may limit the extent of conjugation include:
(i) repeat units that are twisted out of the plane of adjacent repeat units, limiting the extent of p-orbital overlap between adjacent repeat units;
(ii) conjugation-breaking repeat units that do not provide a conjugation path between repeat units adjacent to the conjugation breaking repeat units; and
(iii) repeat units that are linked to adjacent repeat units through positions that limit the extent of conjugation between repeat units adjacent to the repeat unit.

One preferred class of arylene repeat units is phenylene repeat units, such as phenylene repeat units of formula (III):

wherein p in each occurrence is independently 0, 1, 2, 3 or 4, optionally 1 or 2; n is 1, 2 or 3; and $R^1$ independently in each occurrence is a substituent.

Where present, each $R^1$ may independently be selected from the group consisting of:
alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F;
aryl and heteroaryl groups that may be unsubstituted or substituted with one or more substituents, preferably phenyl substituted with one or more $C_{1-20}$ alkyl groups;
a linear or branched chain of aryl or heteroaryl groups, each of which groups may independently be substituted, for example a group of formula —$(Ar^3)_r$ wherein each $Ar^3$ is independently an aryl or heteroaryl group and r is at least 2, preferably a branched or linear chain of phenyl groups each of which may be unsubstituted or substituted with one or more $C_{1-20}$ alkyl groups; and
a crosslinkable-group, for example a group comprising a double bond such and a vinyl or acrylate group, or a benzocyclobutane group.

Substituted N, where present, may be —$NR^2$— wherein $R^2$ is $C_{1-20}$ alkyl; unsubstituted phenyl; or phenyl substituted with one or more $C_{1-20}$ alkyl groups.

Preferably, each $R^1$ is independently selected from $C_{1-40}$ hydrocarbyl, and is more preferably selected from $C_{1-20}$ alkyl; unsubstituted phenyl; and phenyl substituted with one or more $C_{1-20}$ alkyl groups.

If n is 1 then exemplary repeat units of formula (III) include the following:

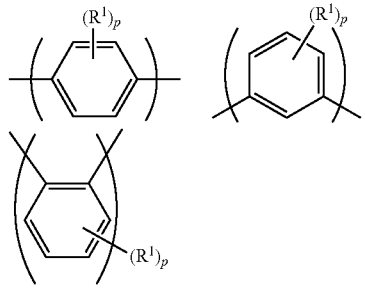

If the repeat unit of formula (III) is 1,4-linked and if p is 0 then the extent of conjugation of repeat unit of formula (III) to one or both adjacent repeat units may be relatively high.

If p is at least 1, and/or the repeat unit is 1,2- or 1,3 linked, then the extent of conjugation of repeat unit of formula (III)

to one or both adjacent repeat units may be relatively low. In one preferred arrangement, the repeat unit of formula (III) is 1,3-linked and p is 0, 1, 2 or 3. In another preferred arrangement, the repeat unit of formula (III) has formula (IIIa):

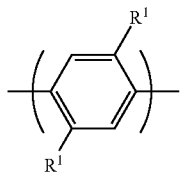

(IIIa)

Substituents $R^1$ of formula (IIIa) are adjacent to linking positions of the repeat unit, which may cause steric hindrance between the repeat unit of formula (IIIa) and adjacent repeat units, resulting in the repeat unit of formula (IIIa) twisting out of plane relative to one or both adjacent repeat units.

Exemplary repeat units where n is 2 or 3 include the following:

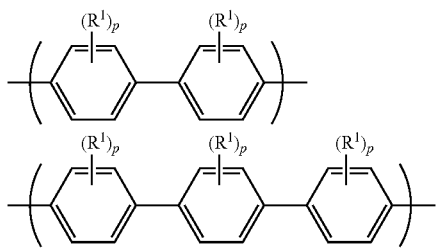

A preferred repeat unit has formula (IIIb):

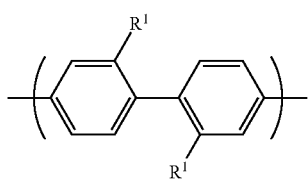

(IIIb)

The two $R^1$ groups of formula (IIIb) may cause steric hindrance between the phenyl rings they are bound to, resulting in twisting of the two phenyl rings relative to one another.

A further class of arylene repeat units are optionally substituted fluorene repeat units, such as repeat units of formula (IV):

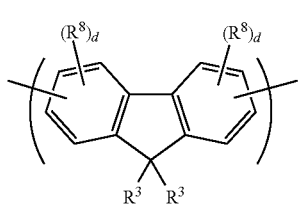

(IV)

wherein $R^3$ in each occurrence is the same or different and is H or a substituent, and wherein the two groups $R^3$ may be linked to form a ring; $R^8$ is a substituent; and d is 0, 1, 2 or 3.

Each $R^3$ is preferably a substituent, and each $R^3$ may independently be selected from the group consisting of:
  alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F;
  aryl or heteroaryl that may be unsubstituted or substituted with one or more substituents;
  a linear or branched chain of aryl or heteroaryl groups, each of which groups may independently be substituted, for example a group of formula —$(Ar^3)_r$— as described below with reference to formula (III); and
  a crosslinkable-group, for example a group comprising a double bond such and a vinyl or acrylate group, or a benzocyclobutane group.

In the case where $R^3$ comprises an aryl or heteroaryl group, or a linear or branched chain of aryl or heteroaryl groups, the or each aryl or heteroaryl group may be substituted with one or more substituents $R^4$ selected from the group consisting of:
  alkyl, for example $C_{1-20}$ alkyl, wherein one or more non-adjacent C atoms may be replaced with O, S, substituted N, C=O and —COO— and one or more H atoms of the alkyl group may be replaced with F;
  $NR^5_2$, $OR^5$, $SR^5$, and
  fluorine, nitro and cyano;
  wherein each $R^5$ is independently selected from the group consisting of alkyl, preferably $C_{1-20}$ alkyl; and aryl or heteroaryl, preferably phenyl, optionally substituted with one or more $C_{1-20}$ alkyl groups.

The aromatic carbon atoms of the fluorene repeat unit may be unsubstituted, or may be substituted with one or more substituents $R^8$. Exemplary substituents $R^8$ are alkyl, for example $C_{1-20}$ alkyl, wherein one or more non-adjacent C atoms may be replaced with O, S, NH or substituted N, C=O and —COO—, optionally substituted aryl, optionally substituted heteroaryl, alkoxy, alkylthio, fluorine, cyano and arylalkyl. Particularly preferred substituents include $C_{1-20}$ alkyl and substituted or unsubstituted aryl, for example phenyl. Optional substituents for the aryl include one or more $C_{1-20}$ alkyl groups.

Substituted N, where present, may be —$NR^2$— wherein $R^2$ is $C_{1-20}$ alkyl; unsubstituted phenyl; or phenyl substituted with one or more $C_{1-20}$ alkyl groups.

Preferably, each $R^3$ is independently selected from $C_{1-40}$ hydrocarbyl, and is more preferably selected from $C_{1-20}$ alkyl; unsubstituted phenyl; phenyl substituted with one or more $C_{1-20}$ alkyl groups; a linear or branched chain of phenyl groups, wherein each phenyl may be unsubstituted or substituted with one or more substituents; and a crosslinkable group.

The repeat unit of formula (IV) may be an optionally substituted 2,7-linked repeat unit of formula (IVa):

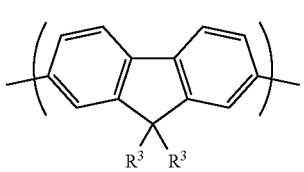

(IVa)

Optionally, the repeat unit of formula (IVa) is not substituted in a position adjacent to the 2- or 7-positions.

The extent of conjugation of repeat units of formulae (IV) may be limited by (a) linking the repeat unit through the 3- and/or 6-positions to limit the extent of conjugation across the repeat unit, and/or (b) substituting the repeat unit with one or more further substituents $R^1$ in or more positions adjacent to the linking positions in order to create a twist with the adjacent repeat unit or units, for example a 2,7-linked fluorene carrying a $C_{1-20}$ alkyl substituent in one or both of the 3- and 6-positions.

Another exemplary arylene repeat unit has formula (V):

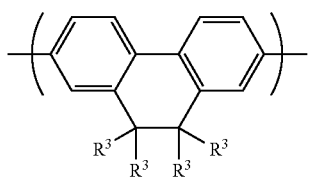
(V)

wherein $R^3$ is as described with reference to formula (IV) above. Any of the $R^3$ groups may be linked to any other of the $R^3$ groups to form a ring. Aromatic carbon atoms of the repeat unit of formula (V) may be unsubstituted, or may be substituted with one or more substituents. Exemplary substituents are alkyl, for example $C_{1-20}$ alkyl, wherein one or more non-adjacent C atoms may be replaced with O, S, NH or substituted N, C=O and —COO—, optionally substituted aryl, optionally substituted heteroaryl, alkoxy, alkylthio, fluorine, cyano and arylalkyl. Particularly preferred substituents include $C_{1-20}$ alkyl and substituted or unsubstituted aryl, for example phenyl. Optional substituents for the aryl include one or more $C_{1-20}$ alkyl groups. Further arylene co-repeat units include: phenanthrene repeat units; naphthalene repeat units; anthracene repeat units; and perylene repeat units. Each of these arylene repeat units may be linked to adjacent repeat units through any two of the aromatic carbon atoms of these units. Specific exemplary linkages include 9,10-anthracene; 2,6-anthracene; 1,4-naphthalene; 2,6-naphthalene; 2,7-phenanthrene; and 2,5-perylene. Each of these repeat units may be substituted or unsubstituted, for example substituted with one or more $C_{1-40}$ hydrocarbyl groups. Co-repeat units may contain only aromatic or heteroaromatic groups in the repeat unit backbone, for example as described above with respect to formulae (III), (IV) and (V), or may contain non-aromatic or heteroaromatic groups in the repeat unit backbone, for example a repeat unit of formula (XII):

—(Ar$^{11}$-Sp$^1$-Ar$^{11}$)—    (XII)

$Ar^{11}$ in each occurrence independently represents a substituted or unsubstituted aryl or heteroaryl group; and $Sp^1$ represents a spacer group that does not provide any conjugation path between the two groups $Ar^{11}$.

$Sp^1$ may contain a single non-conjugating atom only between the two groups $Ar^{11}$, or $Sp^1$ may contain non-conjugating chain of at least 2 atoms separating the two groups $Ar^{11}$.

A non-conjugating atom may be, for example, —O—, —S—, —CR$^{10}_2$— or —SiR$^{10}_2$— wherein $R^{10}$ in each occurrence is H or a substituent, optionally $C_{1-20}$ alkyl.

A spacer chain $Sp^1$ may contain two or more atoms separating the two groups $Ar^{11}$, for example a $C_{1-20}$ alkyl chain wherein one or more non-adjacent C atoms of the chain may be replaced with O or S. Preferably, the spacer chain $Sp^1$ contains at least one sp$^3$-hybridised carbon atom separating the two groups $Ar^{11}$.

Preferred groups $Sp^1$ are selected from $C_{1-20}$ alkyl wherein one or more non-adjacent C atoms are replaced with O.

Exemplary non-conjugating repeat units include the following, each of which may be unsubstituted or substituted with one or more substituents, optionally $C_{1-40}$ hydrocarbyl, for example $C_{1-20}$ alkyl; unsubstituted phenyl; and phenyl substituted with one or more $C_{1-20}$ alkyl groups:

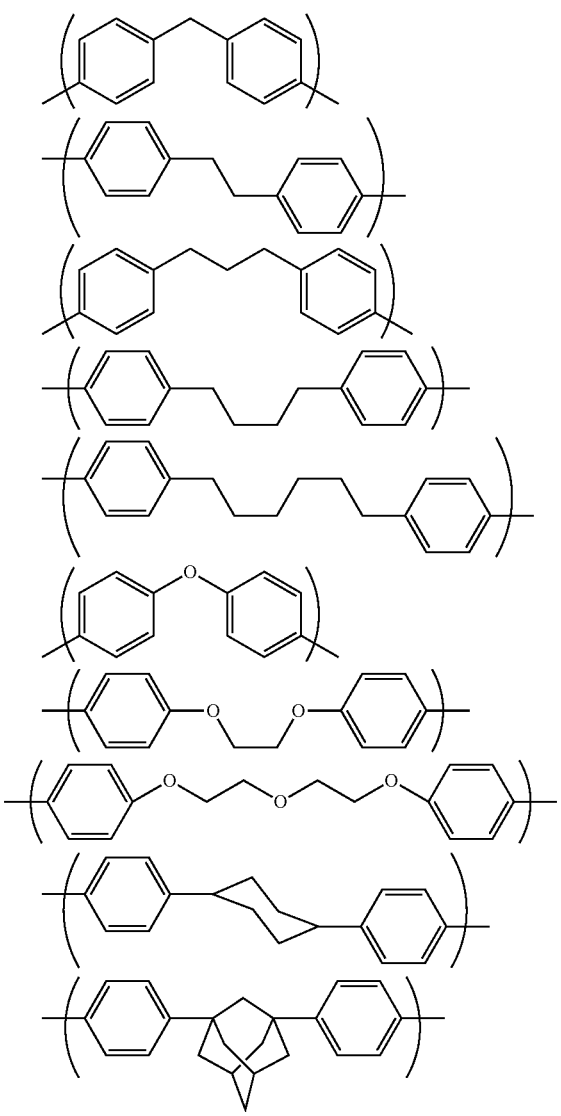

Non conjugating repeat units may make up to 20 mol % of the repeat units of the polymer, optionally up to 10 mol % or up to 5 mol %.

Polymer Synthesis

Preferred methods for preparation of at least partially conjugated polymers, such as a homopolymer or copolymer comprising repeat units of formula (I) as described above, comprise a "metal insertion" wherein the metal atom of a metal complex catalyst is inserted between an aryl or heteroaryl group and a leaving group of a monomer. Exemplary metal insertion methods are Suzuki polymerisation as described in, for example, WO 00/53656 and Yamamoto polymerisation as described in, for example, T. Yamamoto, "Electrically Conducting And Thermally Stable pi-Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups is used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units illustrated throughout this application may be derived from a monomer carrying suitable leaving groups. Likewise, an end-capping group or side group carrying only one reactive leaving group may be bound to the polymer by reaction of a leaving group at the polymer chain end or side respectively, and monomers containing more than two reactive groups may be used to form branching points in the polymer.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular copolymers may be prepared when both reactive groups of a first monomer are boron and both reactive groups of a second monomer are halogen. Suzuki polymerization may be used to control the locations of repeat units relative to one another. For example, if at least 50 mol % of the monomers of a polymerization mixture consist of boronic acid monomers for forming arylene repeat units and if repeat units of formula (I) are formed from halogenated monomers then all repeat units of formula (I) in the resultant polymer will have adjacent arylene repeat units.

As alternatives to halides, other leaving groups capable of participating in metal insertion include sulfonic acids and sulfonic acid esters such as tosylate, mesylate and triflate.

Light-Emitting Layers

An OLED may contain one or more light-emitting layers. A light-emitting layer may contain a polymer comprising repeat units of formula (I).

Suitable light-emitting materials for a light-emitting layer include polymeric, small molecule and dendrimeric light-emitting materials, each of which may be fluorescent or phosphorescent.

A light-emitting layer of an OLED may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display.

A light-emitting layer may contain a mixture of more than one light-emitting material, for example a mixture of light-emitting materials that together provide white light emission.

A blue light emitting material may have a photoluminescent spectrum with a peak in the range of 400-490 nm.

A green light emitting material may have a photoluminescent spectrum with a peak in the range of more than 490 nm up to 580 nm.

A red light emitting material may optionally have a peak in its photoluminescent spectrum of more than 580 nm up to 650 nm, preferably 600-630 nm.

Exemplary fluorescent polymeric light-emitting materials include polymers comprising one or more of arylene repeat units, arylene vinylene repeat units and arylamine repeat units.

Exemplary arylene repeat units are as described above, for example units of formulae (III), (IV) and (V). Exemplary arylamine repeat units have formula (VI):

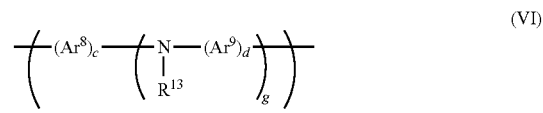

(VI)

wherein $Ar^8$ and $Ar^9$ in each occurrence are independently selected from substituted or unsubstituted aryl or heteroaryl, g is greater than or equal to 1, preferably 1 or 2, $R^{13}$ is H or a substituent, preferably a substituent, and c and d are each independently 1, 2 or 3.

$R^{13}$, which may be the same or different in each occurrence when g>1, is preferably selected from the group consisting of alkyl, for example $C_{1-20}$ alkyl, $Ar^{10}$, a branched or linear chain of $Ar^{10}$ groups, or a crosslinkable unit that is bound directly to the N atom of formula (VI) or spaced apart therefrom by a spacer group, wherein $Ar^{10}$ in each occurrence is independently optionally substituted aryl or heteroaryl. Exemplary spacer groups are $C_{1-20}$ alkyl, phenyl and phenyl-$C_{1-20}$ alkyl.

Any of $Ar^8$, $Ar^9$ and, if present, $Ar^{10}$ in the repeat unit of Formula (VI) may be linked by a direct bond or a divalent linking atom or group to another of $Ar^8$, $Ar^9$ and $Ar^{10}$. Preferred divalent linking atoms and groups include O, S; substituted N; and substituted C.

Any of $Ar^8$, $Ar^9$ and, if present, $Ar^{10}$ may be substituted with one or more substituents. Exemplary substituents are substituents $R^5$, wherein each $R^5$ may independently be selected from the group consisting of:

substituted or unsubstituted alkyl, optionally $C_{1-20}$ alkyl, wherein one or more non-adjacent C atoms may be replaced with optionally substituted aryl or heteroaryl, O, S, substituted N, C=O or —COO— and one or more H atoms may be replaced with F; and a crosslinkable group attached directly to the fluorene unit or spaced apart therefrom by a spacer group, for example a group comprising a double bond such and a vinyl or acrylate group, or a benzocyclobutane group.

Preferred repeat units of formula (VI) have formulae 1-3:

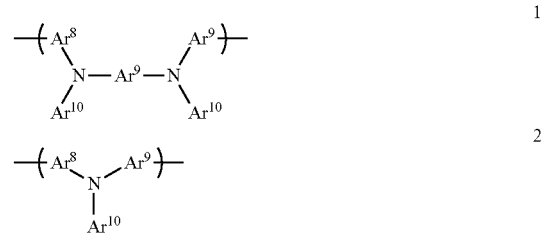

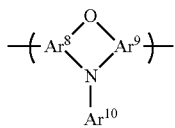

In one preferred arrangement, $R^{13}$ is $Ar^{10}$ and each of $Ar^8$, $Ar^9$ and $Ar^{10}$ are independently and optionally substituted with one or more $C_{1-20}$ alkyl groups. $Ar^8$, $Ar^9$ and $Ar^{10}$ are preferably phenyl.

In another preferred arrangement, $Ar^8$ and $Ar^9$ are phenyl, each of which may be substituted with one or more $C_{1-20}$ alkyl groups, and $R^{13}$ is $—(Ar^{10})_r$, wherein r is at least 2 and wherein the group $—(Ar^{10})_r$ forms a linear or branched chain of aromatic or heteroaromatic groups, for example 3,5-diphenylbenzene wherein each phenyl may be substituted with one or more $C_{1-20}$ alkyl groups.

In another preferred arrangement, c, d and g are each 1 and $Ar^8$ and $Ar^9$ are phenyl linked by an oxygen atom to form a phenoxazine ring.

Amine repeat units may be provided in a molar amount in the range of about 0.5 mol % up to about 50 mol %, optionally about 1-25 mol %, optionally about 1-10 mol %.

Amine repeat units may provide hole-transporting and/or light-emitting functionality.

Preferred light-emitting polymers are copolymers comprising one or more arylene repeat units selected from formulae (III), (IV) and (V) and one or more amine repeat units of formula (VI).

Exemplary phosphorescent light-emitting materials include metal complexes comprising substituted or unsubstituted complexes of formula (IX):

$$ML^1_q L^2_r L^3_s \qquad (IX)$$

wherein M is a metal; each of $L^1$, $L^2$ and $L^3$ is a coordinating group; q is an integer; r and s are each independently 0 or an integer; and the sum of (a. q)+(b. r)+(c.s) is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet or higher states. Suitable heavy metals M include d-block metals, in particular those in rows 2 and 3 i.e. elements 39 to 48 and 72 to 80, in particular ruthenium, rhodium, palladium, rhenium, osmium, iridium, platinum and gold. Iridium is particularly preferred.

Exemplary ligands $L^1$, $L^2$ and $L^3$ include carbon or nitrogen donors such as porphyrin or bidentate ligands of formula (X):

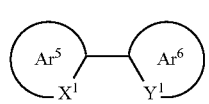

(X)

wherein $Ar^5$ and $Ar^6$ may be the same or different and are independently selected from substituted or unsubstituted aryl or heteroaryl; $X^1$ and $Y^1$ may be the same or different and are independently selected from carbon or nitrogen; and $Ar^5$ and $Ar^6$ may be fused together. Ligands wherein $X^1$ is carbon and $Y^1$ is nitrogen are preferred, in particular ligands in which $Ar^5$ is a single ring or fused heteroaromatic of N and C atoms only, for example pyridyl or isoquinoline, and $Ar^6$ is a single ring or fused aromatic, for example phenyl or naphthyl.

Examples of bidentate ligands are illustrated below:

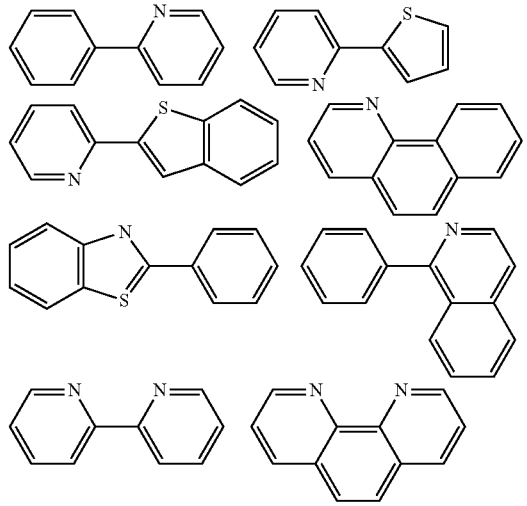

Each of $Ar^5$ and $Ar^6$ may carry one or more substituents. Two or more of these substituents may be linked to form a ring, for example an aromatic ring.

Other ligands suitable for use with d-block elements include diketonates, in particular acetylacetonate (acac); triarylphosphines and pyridine, each of which may be substituted.

Exemplary substituents include groups $R^{13}$ as described above with reference to Formula (VI). Particularly preferred substituents include fluorine or trifluoromethyl which may be used to blue-shift the emission of the complex, for example as disclosed in WO 02/45466, WO 02/44189, US 2002-117662 and US 2002-182441; alkyl or alkoxy groups, for example $C_{1-20}$ alkyl or alkoxy, which may be as disclosed in JP 2002-324679; carbazole which may be used to assist hole transport to the complex when used as an emissive material, for example as disclosed in WO 02/81448; bromine, chlorine or iodine which can serve to functionalise the ligand for attachment of further groups, for example as disclosed in WO 02/68435 and EP 1245659; and dendrons which may be used to obtain or enhance solution processability of the metal complex, for example as disclosed in WO 02/66552.

A light-emitting dendrimer typically comprises a light-emitting core bound to one or more dendrons, wherein each dendron comprises a branching point and two or more dendritic branches. Preferably, the dendron is at least partially conjugated, and at least one of the branching points and dendritic branches comprises an aryl or heteroaryl group, for example a phenyl group. In one arrangement, the branching point group and the branching groups are all phenyl, and each phenyl may independently be substituted with one or more substituents, for example alkyl or alkoxy.

A dendron may have optionally substituted formula (XI)

(XI)

wherein BP represents a branching point for attachment to a core and $G_1$ represents first generation branching groups.

The dendron may be a first, second, third or higher generation dendron. $G_1$ may be substituted with two or more second generation branching groups $G_2$, and so on, as in optionally substituted formula (XIa):

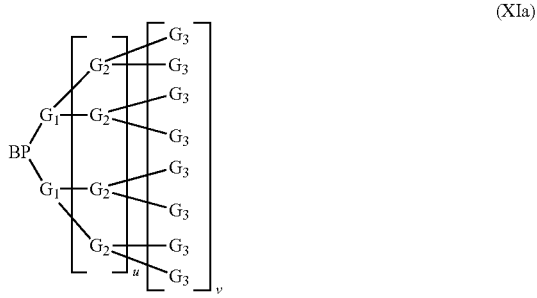

(XIa)

wherein u is 0 or 1; v is 0 if u is 0 or may be 0 or 1 if u is 1; BP represents a branching point for attachment to a core and $G_1$, $G_2$ and $G_3$ represent first, second and third generation dendron branching groups. In one preferred embodiment, each of BP and $G_1$, $G_2$ . . . $G_n$ is phenyl, and each phenyl BP, $G_1$, $G_2$ . . . $G_{n-1}$ is a 3,5-linked phenyl.

A preferred dendron is a substituted or unsubstituted dendron of formula (XIb):

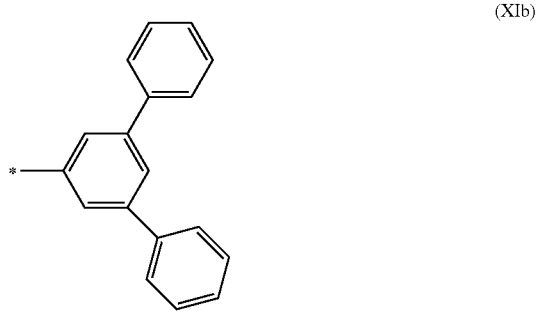

(XIb)

wherein * represents an attachment point of the dendron to a core.

BP and/or any group G may be substituted with one or more substituents, for example one or more $C_{1-20}$ alkyl or alkoxy groups.

Phosphorescent light-emitting materials may be provided in a light-emitting layer with a host material. The host preferably has a triplet energy level that is no more than 0.1 eV lower than that of the phosphorescent light-emitting material, more preferably a triplet energy level that the same as or higher than that of the phosphorescent light-emitting material.

Suitable host materials include small molecule, dendrimeric and polymeric host materials. Polymeric host materials include non-conjugated polymers with pendant charge-transporting groups, for example polyvinylcarbazole, and at least partially conjugated polymers, for example polymers comprising one or both of arylene repeat units and amine repeat units, for example arylene repeat units of formula (III), (IV) and (V) and amine repeat units of formula (VI).

Phosphorescent light-emitting materials may make up about 0.05 mol % up to about 20 mol %, optionally about 0.1-10 mol % of a host/phosphorescent light-emitting material composition.

The phosphorescent light-emitting material may be physically mixed with the host material or may be covalently bound thereto. In the case of a polymeric host, the phosphorescent light-emitting material may be provided in a side-chain, main chain or end-group of the polymer. Where the phosphorescent material is provided in a polymer side-chain, the phosphorescent material may be directly bound to the backbone of the polymer or spaced apart therefrom by a spacer group, for example a $C_{1-20}$ alkyl spacer group in which one or more non-adjacent C atoms may be replaced by O or S.

Hole Injection Layers

A conductive hole injection layer, which may be formed from a conductive organic or inorganic material, may be provided between the anode and the light-emitting layer or layers of an OLED to improve hole injection from the anode into the layer or layers of semiconducting polymer. Examples of doped organic hole injection materials include optionally substituted, doped poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. No. 5,723,873 and U.S. Pat. No. 5,798,170; and optionally substituted polythiophene or poly (thienothiophene). Examples of conductive inorganic materials include transition metal oxides such as VOx MoOx and RuOx as disclosed in Journal of Physics D: Applied Physics (1996), 29(11), 2750-2753.

Where a hole-transporting layer is present, a hole-injection layer may be provided between the anode and the hole-transporting layer.

Charge Transporting and Charge Blocking Layers

A hole transporting layer may be provided between the anode and the light-emitting layer or layers, as described above. Likewise, an electron transporting layer may be provided between the cathode and the light-emitting layer or layers.

Similarly, an electron blocking layer may be provided between the anode and the light-emitting layer and a hole blocking layer may be provided between the cathode and the light-emitting layer. Transporting and blocking layers may be used in combination. Depending on its HOMO and LUMO levels, a single layer may both transport one of holes and electrons and block the other of holes and electrons.

If present, a hole transporting layer located between the anode and the light-emitting layers preferably has a HOMO level of less than or equal to 5.5 eV, more preferably around 4.8-5.5 eV as measured by cyclic voltammetry. The HOMO level of the hole transport layer may be selected so as to be within 0.2 eV, optionally within 0.1 eV, of an adjacent layer (such as a light-emitting layer) in order to provide a small barrier to hole transport between these layers. The hole-transporting layer may be a polymer comprising repeat units of formula (I) as described above.

If present, an electron transporting layer located between the light-emitting layers and cathode preferably has a LUMO level of around 2.5-3.5 eV as measured by square wave cyclic voltammetry. For example, a layer of a silicon monoxide or silicon dioxide or other thin dielectric layer having thickness in the range of 0.2-2 nm may be provided between the light-emitting layer nearest the cathode and the cathode. HOMO and LUMO levels may be measured using cyclic voltammetry.

An electron transporting layer may contain a polymer comprising a chain of optionally substituted arylene repeat units, such as a chain of fluorene repeat units.

Cathode

The cathode is selected from materials that have a workfunction allowing injection of electrons into the light-emitting layer. Other factors influence the selection of the cathode such as the possibility of adverse interactions between the cathode and the light-emitting material. The cathode may consist of a single material such as a layer of aluminium. Alternatively, it may comprise a plurality of conductive materials, for example a plurality of conductive metals such a bilayer of a low workfunction material and a high workfunction material such as calcium and aluminium as disclosed in WO 98/10621. The cathode may comprise a layer of elemental barium, for example as disclosed in WO 98/57381, Appl. Phys. Lett. 2002, 81(4), 634 and WO 02/84759. The cathode may comprise a thin (e.g. less than 5 nm) layer of metal compound between the organic semiconducting layers and one or more conductive cathode layers, in particular an oxide or fluoride of an alkali or alkali earth metal, to assist electron injection, for example lithium fluoride, for example as disclosed in WO 00/48258; barium fluoride, for example as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Formulation Processing

Polymers comprising repeat units of formula (I) may be dispersed or dissolved in a solvent or mixture of two or more solvents to form a formulation that may be used to form a layer containing the compound by depositing the formulation and evaporating the solvent or solvents. The formulation may contain one or more further materials in addition to the polymer. All of the components of the formulation may be dissolved in the solvent or solvent mixture, in which case the formulation is a solution, or one or more components may be dispersed in the solvent or solvent mixture. Preferably, the formulation is a solution. Exemplary solvents for polymers comprising repeat units of formula (I) are mono- and poly-alkylated benzene, for example toluene and xylenes.

Techniques for forming layers from a formulation include printing and coating techniques such spin-coating, dip-coating, roll printing, screen printing and inkjet printing.

Multiple organic layers of an OLED may be formed by deposition of formulations containing the active materials for each layer.

During OLED formation, a layer of the device may be crosslinked to prevent it from partially or completely dissolving in the solvent or solvents used to deposit an overlying layer. Where used as a hole-transporting layer, polymers comprising repeat units of formula (I) may be crosslinked following deposition prior to deposition of an overlying layer.

Suitable crosslinkable groups include groups comprising a reactive double bond such and a vinyl or acrylate group, or a benzocyclobutane group.

Coating methods such as spin-coating are particularly suitable for devices wherein patterning of the light-emitting layer is unnecessary—for example for lighting applications or simple monochrome segmented displays.

Printing methods such as inkjet printing are particularly suitable for high information content displays, in particular full colour displays. A device may be inkjet printed by providing a patterned layer over the first electrode and defining wells for printing of one colour (in the case of a monochrome device) or multiple colours (in the case of a multicolour, in particular full colour device). Each well may define a pixel area, and each pixel may be subdivided into subpixels. The patterned layer may be a layer of photoresist that is patterned to define wells as described in, for example, EP 0880303.

As an alternative to wells, the formulation may be printed into channels defined within a patterned layer. In particular, the photoresist may be patterned to form channels which, unlike wells, extend over a plurality of pixels and which may be closed or open at the channel ends.

EXAMPLES

Monomer Example 1

Monomer Example 1 was prepared according to the following reaction scheme:

Scheme 1

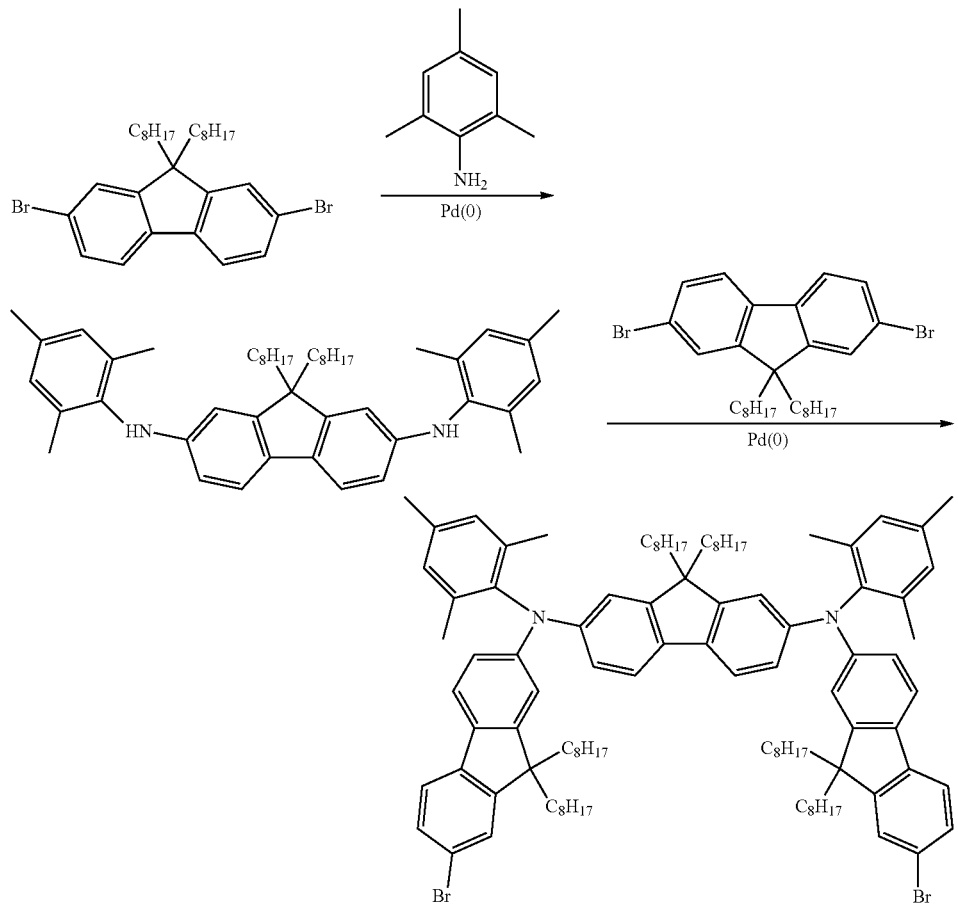

STAGE 1: 2,7-dibromo-9-dioctylfluorene (115 g, 210 mmol) and trimethyl aniline (62.4 g, 461 mmol) were charged to a 5 L flask, equipped with a mechanical stirrer, a condenser and nitrogen inlet. The mixture was sparged with nitrogen for 90 minutes. Tris(dibenzylideneacetone)dipalladium(0) (0.96 g, 1.05 mmol) and tri-tert-butyl-phosphonium tetrafluoroboronate (0.46 g, 1.5 mmol) were added and the mixture was sparged for a further 15 minutes. Sodium tert-butoxide (60.49 g, 629 mmol) was added portion-wise added and the mixture was sparged for a further 5 minutes. The reaction mixture was heated to reflux for 24 hours. After cooling to room temperature, the mixture was quenched with water (400 ml). The aqueous phase was further extracted with toluene and the combined organic phases were reduced to dryness to give a dark brown oil. This was dissolved in toluene (500 ml) passed through a Celite® topped silica plug, rinsing through with toluene. The toluene eluant was reduced to dryness by rotary evaporation. The residue was triturated with methanol to give a solid. Further recrystallisation from isopropanol resulted in the isolation of the product at high purity (113 g, 83% yield).

STAGE 2: A 250 ml round bottomed flask, equipped with a magnetic stirrer, condenser and nitrogen inlet, was charged with the stage 1 material (3.0 g, 4.6 mmol), 9-di-n-octyl-fluorene (15 g, 27.4 mmol), anhydrous xylene (36 ml) and anhydrous tetrahydrofuran (24 ml). The mixture was sparged with nitrogen for 15 minutes, before tris(dibenzylideneacetone)dipalladium(0) (0.0.083 g, 0.092 mmol) and 1,1'-Bis(diphenylphosphino)ferrocene (0.202 g, 0.36 mmol) were added. The mixture was sparged with nitrogen for 10 minutes, before sodium t-butoxide (1.76 g, 18.3 mmol) was added. The reaction mixture was heated to reflux for 3 hours.

After cooling to room temperature, water (100 ml) was added to quench the reaction and the product extracted with toluene. The organic extracts were removed under rotary evaporation. The residue was precipitated from dichlormethane and acetonitrile (2:5) to give a light yellow powder. This was further purified by repeated column chromatography to yield the target compound (1.1 g, 16% yield).

Polymer Example 1

Polymer Example 1 was prepared by Suzuki polymerisation as described in WO 00/53656 of the following monomers:

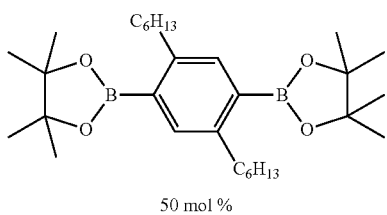

50 mol %

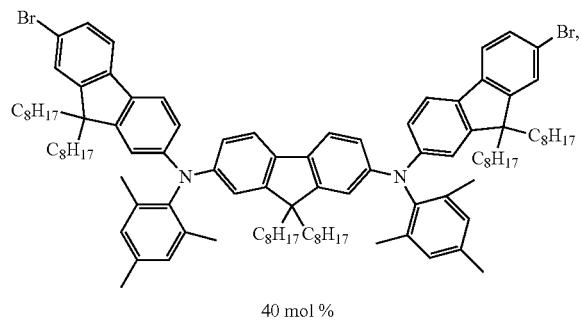

40 mol %

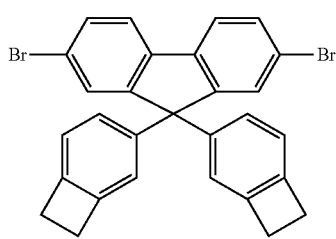

5 mol %

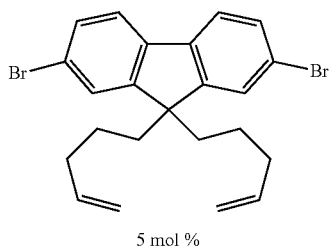

5 mol %

The polymer had a weight average molecular weight of 382,000, a peak molecular weight of 275,000, a number average molecular weight of 60,000 and a polydispersity of 6.32.

Polymer Example 2

A polymer was prepared as described in Polymer Example 1, except that 30 mol % of Monomer Example 1 and 10 mol % of 2,7-dibromo-9,9-di(n-octyl)fluorene was used for polymerisation in place of 40 mol % of Monomer Example 1, and the boronic ester monomer of Polymer Example 1 was replaced with 50 mol % of the following monomer:

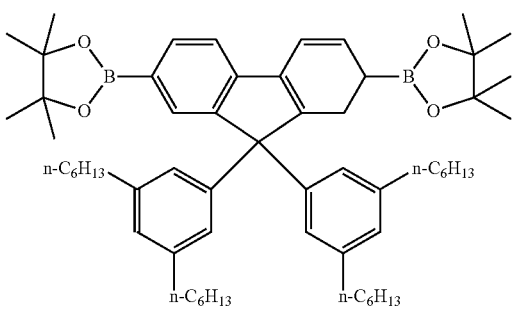

Monomer Example 1

The polymer had a weight average molecular weight of 1,572,000, a peak molecular weight of 1,065,000, a number average molecular weight of 125,000 and a polydispersity of 12.59.

Comparative Polymer 1

For the purpose of comparison, Comparative Polymer 1 was prepared as described with respect to Polymer Example 1 except that Monomer Example 1 was replaced with Comparative Monomer 1, illustrated below.

Comparative Monomer 1

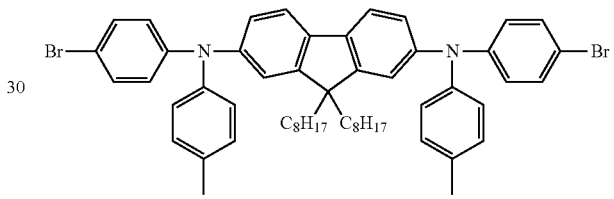

The polymer had a weight average molecular weight of 164,000, a peak molecular weight of 143,000, a number average molecular weight of 32,000 and a polydispersity of 5.19.

DEVICE EXAMPLES

General Device Process

An organic light-emitting device having the following structure was prepared:

ITO/HIL/HTL/LE/Cathode wherein ITO is an indium-tin oxide anode; HIL is a hole-injecting layer, HTL is a hole-transporting layer and LE is a light-emitting layer.

A substrate carrying ITO was cleaned using UV/Ozone. The hole injection layer was formed by spin-coating an aqueous formulation of a hole-injection material available from Plextronics, Inc. A hole transporting layer was formed to a thickness of 22 nm by spin-coating a hole-transporting polymer and crosslinking the polymer by heating. A light-emitting layer was formed to a thickness of 65 nm by spin-coating. A cathode was formed by evaporation of a first layer of a metal fluoride to a thickness of about 2 nm, a second layer of aluminium to a thickness of about 200 nm and an optional third layer of silver.

Blue Device Example 1

A device was prepared according to the General Device Process wherein the hole-transporting layer was formed by spin-coating Polymer Example 1 from a mixed xylenes solution, and a blue fluorescent light-emitting layer was formed by spin-coating Blue Polymer 1 and Additive Polymer 1 in a 9:1 molar ratio from mixed xylenes.

Blue Polymer 1 was formed by Suzuki polymerization as described in WO 00/53656 of the following monomers:

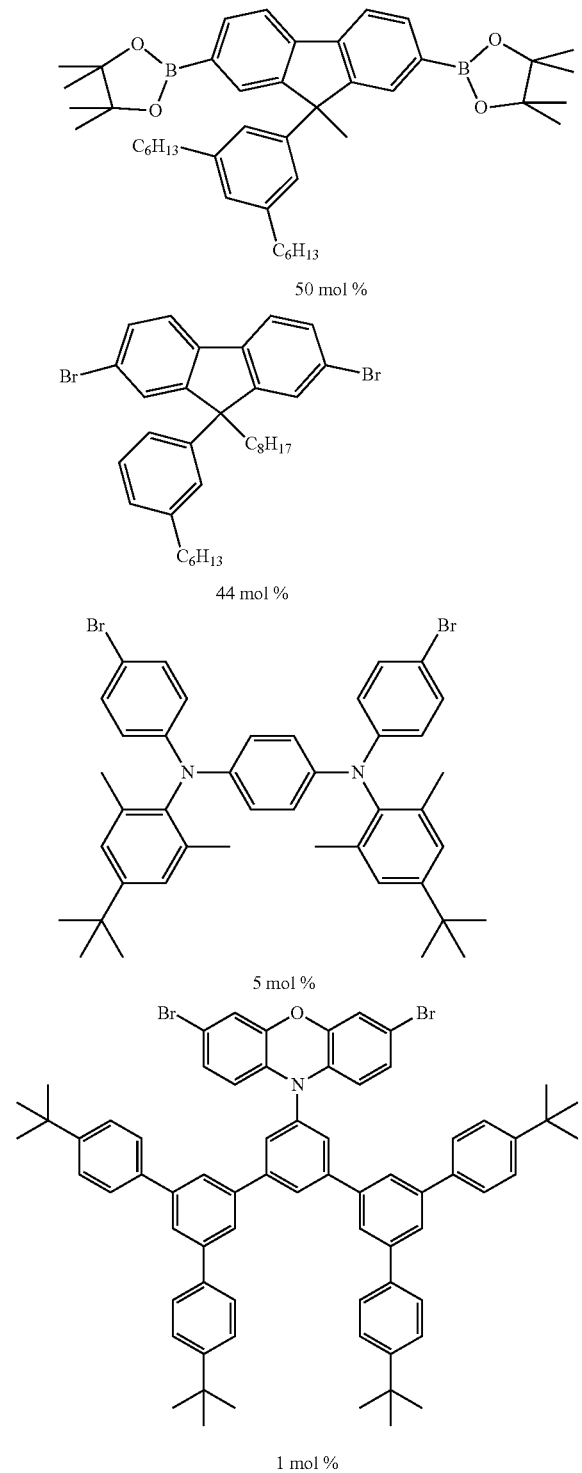

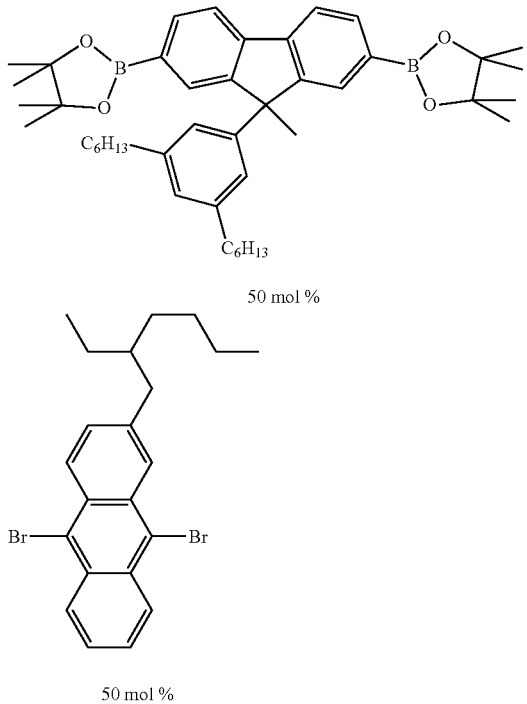

Additive Polymer 1 was formed by Suzuki polymerization as described in WO 00/53656 of the following monomers:

Comparative Blue Device

A blue light emitting OLED was prepared as described in Blue Device Example 1 except that the hole-transporting layer was formed by spin-coating Comparative Polymer 1.

Data for the two devices is provided in Table 1 below, in which CIE y is the y-coordinate of light emitted from the device on the CIE 1931 colour space, and T60 and T50 are the times taken for luminance the device to decay to 60% and 50% of an initial luminance at constant current from a starting luminance of 5,000 cd/m$^2$.

TABLE 1

| Device | CIE-y | Voltage at 10 mA/cm$^2$ | EQE % | T50 (hours) | T60 (hours) |
|---|---|---|---|---|---|
| Blue Device Example 1 | 0.120 | 8.3 | 8.5 | 250* | 145 |
| Comparative Blue Device | 0.117 | 8.7 | 9.0 | 60 | 45 |

*estimated from data after 160 hours.

It can be seen that both T60 and T50 values of Blue Device Example 1 are much larger than those of the Comparative Blue Device.

Blue Device Example 2

A device was prepared according to the General Device Process wherein the hole-transporting layer was formed by spin-coating Polymer Example 1, and a blue fluorescent light-emitting layer was formed by spin-coating Blue Polymer 1: Additive Polymer 1 in a 9:1 molar ratio from mixed xylenes.

Blue Device Example 3

A device was prepared according to Blue Device Example 2 except that the hole transporting layer was formed by spin-coating Polymer Example 2.

Data for the Blue Device Examples 2 and 3 are provided in Table 2.

TABLE 2

| Device | CIE-y | Voltage at 10 mA/cm² | EQE, % | T50 (corrected) |
|---|---|---|---|---|
| Blue Device Example 2 | 0.142 | 3.97 | 8.0 | 260 |
| Blue Device Example 3 | 0.142 | 4.04 | 6.25 | 287 |

Phosphorescent Device Example

A device was prepared according to the General Device Process wherein the hole-transporting layer was formed by spin-coating Polymer Example 1, and the light-emitting layer was formed by spin-coating a host polymer system and phosphorescent emitter 1:

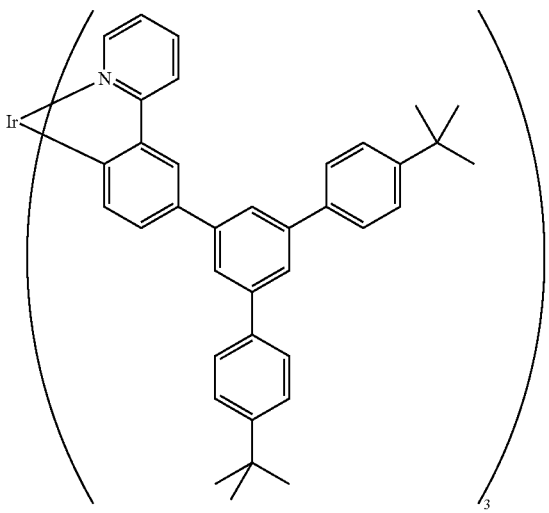

Phosphorescent Emitter 1

Comparative Phosphorescent Device

A device was prepared as described for the Phosphorescent Device Example, except that Comparative Polymer 1 was used in place of Polymer Example 1.

Data for the phosphorescent devices are provided in Table 3.

TABLE 3

| Device | CIE-y | Voltage at 10 mA/cm² | EQE, % | T60 (hours) |
|---|---|---|---|---|
| Phosphorescent Device Example | 0.634 | 7.4 | 14 | 223 |
| Comparative Phosphorescent Device | 0.634 | 7.1 | 19 | 142 |

T60 of the Phosphorescent Device Example is much larger than that of the Comparative Phosphorescent Device.

Without wishing to be bound by any theory, it is believed that the increased lifetime is attributable to increased conjugation around nitrogen atoms of the amine repeat units, which may have a stabilising effect.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. An organic electronic device comprising an anode, a cathode, a semiconducting layer between the anode and the cathode, and a hole transporting layer between the anode and the semiconducting layer, the hole-transporting layer comprising a co-polymer comprising repeat units of formula (I) and at least two different co-repeat units:

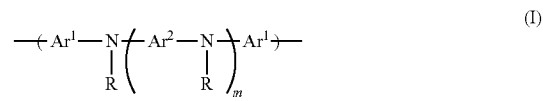

wherein:
Ar² represents an aryl or heteroaryl group that may be unsubstituted or substituted with one or more substituents; R independently in each occurrence represents a substituent; and m is 1 or 2;
each Ar¹ is directly bound to an aromatic or heteroaromatic group of a co-repeat unit; and
Ar¹ is of formula (II):

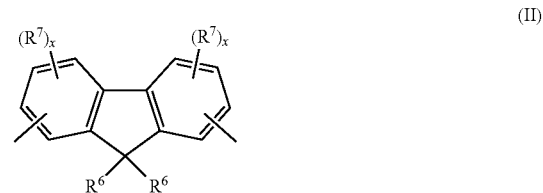

wherein R⁶ in each occurrence is independently H or a substituent; R⁷ in each occurrence is independently a substituent; and x in each occurrence is independently 0, 1, 2 or 3.

2. An organic electronic device according to claim 1 wherein R is an aryl or heteroaryl group that may be unsubstituted or substituted with one or more substituents.

3. An organic electronic device according to claim 1 wherein Ar² is a fused aryl.

4. An organic electronic device according to claim 1 wherein at least one co-repeat unit is an aromatic group that may be unsubstituted or substituted with one or more substituents.

5. An organic electronic device according to claim 4 wherein at least one of the co-repeat units is a repeat unit of formula (III):

wherein p in each occurrence is independently 0, 1, 2, 3 or 4; n is 1, 2 or 3; and R¹ independently in each occurrence is a substituent.

6. An organic electronic device according to claim 4 wherein at least one of the co-repeat units is a repeat unit of formula (IV):

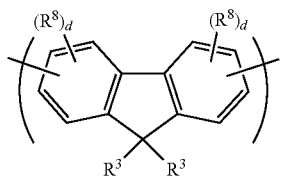

wherein R³ in each occurrence is the same or different and is H or a substituent, and wherein the two groups R³ may be linked to form a ring; R⁸ is a substituent; and d is 0, 1, 2 or 3.

7. An organic electronic device according to claim 1 wherein the co-polymer is crosslinked.

8. An organic electronic device according to claim 1 wherein the device is an organic light-emitting device, and the semiconducting layer is an organic light-emitting layer.

9. An organic electronic device comprising an anode, a cathode, a semiconducting layer between the anode and the cathode, and a hole transporting layer between the anode and the semiconducting layer, the hole-transporting layer comprising a co-polymer comprising repeat units of formula (I) and one or more co-repeat units:

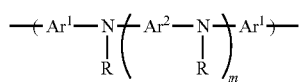

wherein:
Ar² represents an aryl or heteroaryl group that may be unsubstituted or substituted with one or more substituents; R independently in each occurrence represents a substituent; and m is 1or 2;
each Ar¹ is directly bound to an aromatic or heteroaromatic group of a co-repeat unit; and
Ar¹ is of formula (II):

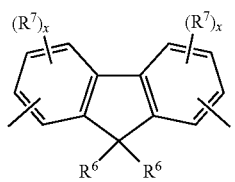

wherein R⁶ in each occurrence is independently H or a substituent; R⁷ in each occurrence is independently a substituent; x in each occurrence is independently 0, 1, 2 or 3;
wherein at least one co-repeat unit is an aromatic group that may be unsubstituted or substituted with one or more substituents; and
wherein at least one of the co-repeat units is a repeat unit of formula (IV):

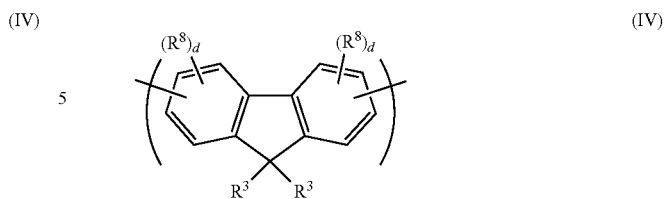

wherein R³ in each occurrence is the same or different and is H or a substituent, and wherein the two groups R³ may be linked to form a ring; R⁸ is a substituent; and d is 0, 1, 2 or 3.

10. An organic electronic device comprising an anode, a cathode, a semiconducting layer between the anode and the cathode, and a hole transporting layer between the anode and the semiconducting layer, the hole-transporting layer comprising a co-polymer comprising repeat units of formula (I) and one or more co-repeat units:

$$-\!\!\!\left(\!Ar^1\!-\!\underset{R}{N}\!\left(\!Ar^2\!-\!\underset{R}{N}\!\right)_{\!m}\!Ar^1\!\right)\!\!\!-$$ (I)

wherein:
Ar² represents an aryl or heteroaryl group that may be unsubstituted or substituted with one or more substituents; R independently in each occurrence represents a substituent; and m is 1or 2;
each Ar¹ is directly bound to an aromatic or heteroaromatic group of a co-repeat unit; and
Ar¹ is of formula (II):

(II)

wherein R⁶ in each occurrence is independently H or a substituent; R⁷ in each occurrence is independently a substituent; x in each occurrence is independently 0, 1, 2 or 3; and
wherein the co-polymer is crosslinked.

11. A method of forming an organic electronic device according to claim 1, the method comprising the steps of: forming the hole-transporting layer over the anode; forming the semiconducting layer over the hole-transporting layer; and forming the cathode over the semiconducting layer.

12. A method according to claim 11 wherein the hole transporting layer is formed by depositing a formulation comprising the polymer comprising repeat units of formula (I) and one or more solvents and evaporating the one or more solvents.

13. A method according to claim 11 wherein the hole-transporting layer is crosslinked prior to formation of the semiconducting layer.

* * * * *